United States Patent [19]
Erb et al.

[11] Patent Number: 6,046,008
[45] Date of Patent: Apr. 4, 2000

[54] IMMUNOLOGICALLY BASED STRIP TEST UTILIZING IONOPHORE MEMBRANES

[75] Inventors: Judith Louise Erb, Ann Arbor; Nallaperumal Chidambaram, Dearborn Heights; James Germain Downward, IV, Ann Arbor, all of Mich.

[73] Assignee: IA, Inc., Ann Arbor, Mich.

[21] Appl. No.: 08/842,075

[22] Filed: Apr. 24, 1997

[51] Int. Cl.[7] .................. G01N 33/53; G01N 33/558; G01N 33/559; C12Q 1/68
[52] U.S. Cl. ................. 435/7.1; 435/6; 435/970; 436/514; 436/515; 436/538; 436/805; 436/810
[58] Field of Search ................. 435/7.1, 6, 970; 436/514, 515, 538, 810, 805

[56] References Cited

U.S. PATENT DOCUMENTS 5,443,955  8/1995  Cornell et al. ..................... 435/7.21

Primary Examiner—James C. Housel
Assistant Examiner—Rodney P. Swartz
Attorney, Agent, or Firm—Kohn & Associates

[57] ABSTRACT

A testing apparatus 10 having an absorbent matrix 12, including a membrane 14 which contains a plurality of counter-ions 16. Chromoionophore (or fluorionophore)s 18 and affinophores 22 compete to carry ions into the membrane 14 and neutralize the charge of the counter-ions 16. Biological recognition molecules 42 bind to a portion of the affinophores 22 and prevent them from entering the membrane 14, thereby allowing more chromoionophore (or fluorionophore)s 18 to enter the membrane 14. The portion of affinophores 22 bound to the biological recognition molecules 42 is inversely proportional to the amount or concentration of analyte 40 occurring within the solution or medium 30. The result of this is that the color of the membrane-covered matrix changes in a manner related to the concentration of the analyte. One application of this apparatus is a strip test for prediction of ovulation.

18 Claims, 5 Drawing Sheets

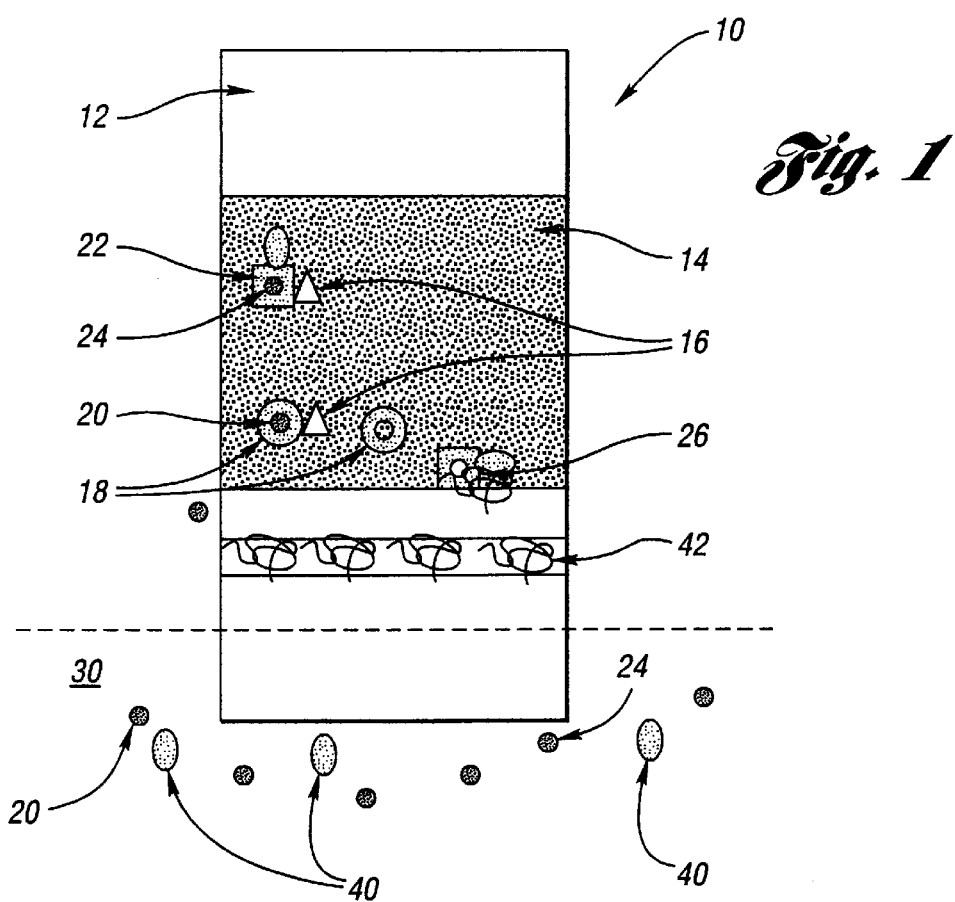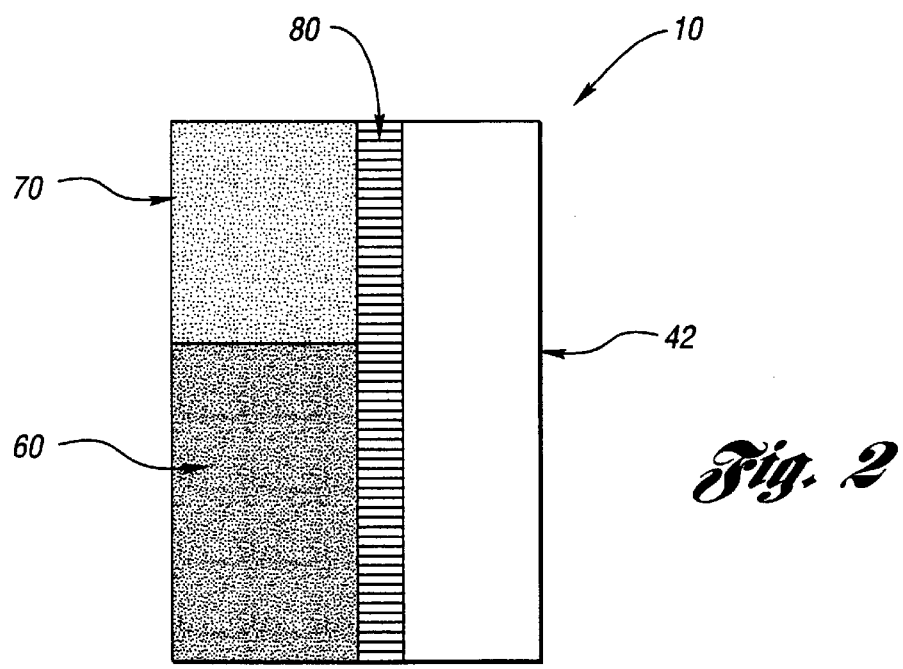

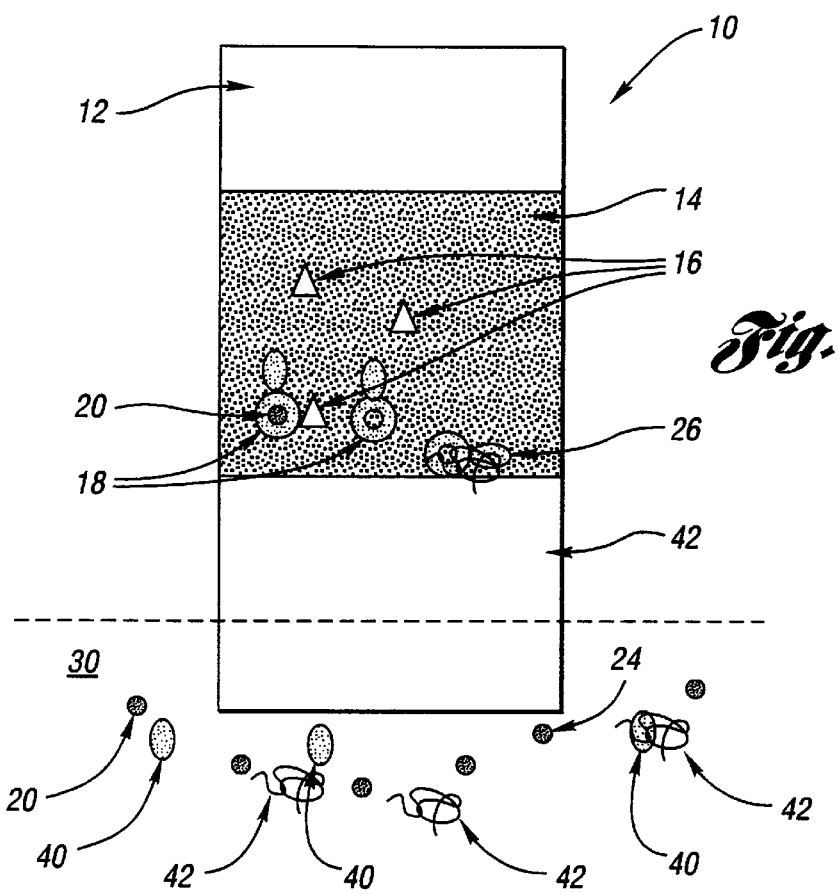
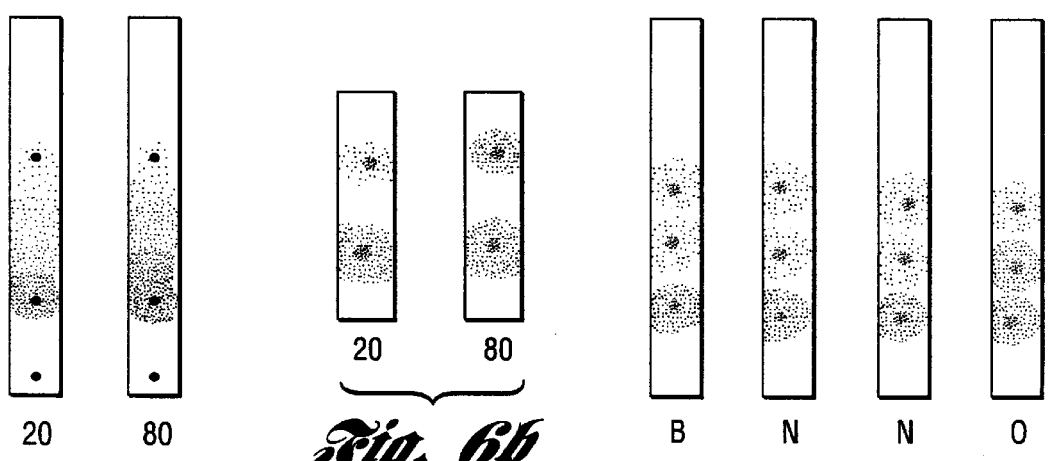

IMMUNOLOGICALLY BASED STRIP TEST UTILIZING IONOPHORE MEMBRANES

The U.S. Government has a nonexclusive, nontransferable, irrevocable paid-up license to practice or have practiced this invention for or on its behalf as provided for by the terms of Contract No. DAMD17-96-C-6026 awarded bt the U.S. Department of the Army.

BACKGROUND OF THE INVENTION

1. Field of the Invention

This invention relates to an apparatus and a methodology to determine the presence and/or concentration of certain metabolites or other substances occurring within a certain medium, such as and without limitation, blood, urine, and saliva. In one embodiment the apparatus and methodology utilizing the principles of the invention is adapted for use as a birth management tool.

2. Background of the Invention

Many types of "home-based" testing apparatuses exist to determine the presence and/or concentration of substances such as metabolites occurring within some medium. While these prior "home-based" testing apparatuses often adequately determine the presence of some of these substances, such as metabolites, they are not capable of determining the concentration or, in many cases, even the presence of such target substances when the concentration of these metabolites or other substances is less than about $10^{-6}$M. In these cases, relatively complex and costly laboratory tests must be done, usually by one or more trained technicians, in order to ascertain the presence and/or concentration of these substances. There is therefore a great need for a technique (hereinafter the term "technique" as used in this Application refers to both an apparatus and a methodology) to reduce health care cost by providing a relatively inexpensive and relatively easy to use "home-based" testing apparatus to determine the presence and/or concentration of certain substances or metabolites. Applicant's invention addresses and fulfills this need. Moreover, there is also a great need for a "real time" diagnostic technique that will provide reliable data concerning the presence and/or concentration of certain metabolites and other substances occurring within a certain medium and which will allow an individual to take a prompt action in response to the diagnostic indications. Applicant's invention provides such a "real time" diagnostic indication.

Particularly, Applicant has found that these various needs are particularly acute in the field of birth control and birth management and that Applicant's invention, in one embodiment, is particularly suited for use in birth control and birth management. That is, it has been deduced form a retrospective study of family planning records that about 90% of all conceptions occur within about a five day period which probably spans the day of the peak concentration of the luteinizing hormone occurring and/or most often sensed within human urine, and more particularly, probably spans from about two days before this peak occurs until about three days after the peak arrives. It is known that during this fertile period, sexual intercourse may lead to pregnancy. Hence, many of the current "home-based" birth management techniques utilize some sort of color changeable paper to notify the users of the pending fertility period by measuring the concentration of the luteinizing hormone. While somewhat useful, these prior techniques provide notification of the impending ovulation no more than thirty-six hours prior to the onset of the fertile period. Since the average longevity of sperm in the vagina is about forty-eight hours, these prior "home-based" tests do not detect the start of the fertility cycle sufficiently early to reliably prevent conception and/or to actually "manage" the conception process.

It is known that the 17-estradiol metabolite, estrone-3-glucuronide (commonly referred to by those of ordinary skill in the art as "E1-g") reaches about 85% to about 95% of its peak value in human urine within about 72 hours prior to the onset of ovulation. Hence, the concentration measurements of E1-g in urine, as Applicant has found, provides a reliable advance warning of the onset of ovulation, sufficient to prevent conception since the time of warning is longer that the lifetime of sperm in the vagina and sufficient to allow individuals to "manage" conception (e.g. actively determine and plan when conception should begin). Prior "home-based" techniques are not readily able to measure E1-g within the urine because the gradual monotonic peak of E1-g requires a more quantitative detection device than current tests provide. Moreover, the World Health Organization has determined the "home-based" E1-g birth management systems would be of great utility in managing the world's population and would be especially useful in overpopulated and developing countries since birth management could be achieved (e.g. birth control could be achieved by abstinence during the ovulation period while conception could be more readily achieved by sexual intercourse during ovulation). Applicant's invention, in one embodiment, provides such an E1-g sensing and/or testing apparatus for use in "home-based" birth management and provides the utility sought in the developing and overpopulated countries. Applicant's invention is therefore an advance in the art of birth management and contains general inventive principles which have a wide use in many other areas of sensing systems.

SUMMARY OF THE INVENTION

It is a first objective of the present invention to provide a rapid measurement technique for determining the presence and/or concentration of certain analytes (metabolites and/or other substances within a medium such as urine, blood, and/or saliva) which overcomes the various disadvantages of the prior art.

It is a second object of the present invention to provide a "home-based" technique to determine the presence and/or concentration of certain analytes and other substances within a medium.

It is a third object of the invention to provide a technique to determine the concentration of the analyte, E1-g, in a medium.

It is a fourth object of the present invention to provide a technique which generates a certain color which is indicative of the concentration of a certain analyte, such as E1-g, within a medium.

It is a fifth object of the present invention to provide a technique to provide for "home-based" birth management in a manner which is superior to that of the prior art.

It is a sixth object of the present invention to provide a technique for measuring the concentration and/or occurrence of a certain target analyte occurring within a medium by the use of first and second substances which compete for entry into a membrane which is constrained to remain electrically neutral.

It is a seventh object of the present invention to provide a technique utilizing a matrix type strip which is adapted for placement within a target medium and which is further adapted to provide a certain color indication at a certain portion thereof, indicative of the concentration of a certain target analyte occurring within the target medium.

It is an eighth object of the present invention to provide a technique utilizing a continuous strip which is adapted for placement within a target medium and which is further adapted to display certain color indication whose position along the strip is indicative of the concentration of a certain target analyte occurring within the target medium.

It is a ninth object of the present invention to provide an affinophore molecule which is synthesized so as to have a certain binding affinity for antibody to estrone 3-glucuronide, which allows the biological recognition molecule to modulate the entry of two competing substances within a membrane by an amount which is proportional to the concentration of a certain third substance within the medium. In general, an affinophore for use in Applicant's techniques is created from a commercially available ionophore which has been chemically and/or biologically altered or conjugated with or to a molecule so as to have a binding affinity for a biological recognition molecule which has a binding affinity for the metabolite or other substance whose concentration is to be measured. The biological recognition molecule may alternatively comprise an antibody, a portion of an antibody, a biological receptor for the analyte, a portion of a nucleotide sequence having chemical and/or biological affinity for the analyte, or virtually any other substance which has some chemical and/or biological binding affinity for the analyte of interest.

According to a first aspect of the present invention, an apparatus to determine the concentration of a certain metabolite occurring within a solution is provided. The apparatus comprises a test strip which changes color in response to the binding of an analyte-specific biological recognition molecule (e.g. an antibody, a receptor, a piece of DNA) or a portion of such a recognition molecule which retains relevant binding characteristics, and its binding partner. The color change results from response of a lipophilized chromophore which changes its color (or fluorescence) in response to the concentration of the specific ion (such as H+). Such a molecule is referred to as a "chromoionophore (or fluorionophore)". The ability of the chromoionophore (or fluorionophore) to sense the true concentration of the specific ion is modulated by the amount of binding of the biological recognition molecule for its binding partner. The mechanism for this modulation of chromoionophore (or fluorionophore) response to the binding between the biological recognition molecule and its binding partner can be direct or indirect as follows:

Direct modulation: The chromoionophore (or fluorionophore) is attached chemically to a molecule having an affinity for the biological recognition molecule. Such a molecule is hereafter referred to as a "chromaffinophore (or fluoraffinophore)". When the recognition molecule binds to the chromaffinophore (or fluoraffinophore), the chromoionophore (or fluorionophore) portion is obstructed by the relatively large biological recognition molecule. This alters the chromaffinophore (or fluoraffinophore)'s ability to interact chemically with the ion to which it specifically responds.

Indirect modulation: The chromoionophore (or fluorionophore) exists in an ion exchange context with a second ionophore which binds a second ion and transports it into a lipophilic environment such as a membrane. Charge neutrality must be maintained within the membrane. To achieve this, the membrane also contains a limited concentration of a lipophilic ion of opposite charge to that of the ions which are transported by the ionophore and chromoionophore (or fluorionophore). Both the chromoionophore (or fluorionophore) and the other ionophore compete for charge neutralization by this counter-ion in carrying their respective ions into the membrane. In the case of indirect modulation, the ionophore is attached chemically to a molecule having an affinity for the biological recognition molecule. Such a molecule is hereafter referred to as an "affinophore". The binding of the recognition molecule to the affinophore alters its ability to transport its specific ion into the membrane. This makes more counter-ion available to the chromoionophore (or fluorionophore) thereby permitting increased transport of its ion into the membrane and causing a shift in the ion concentration at which a color or fluorescence change occurs in the chromoionophore (or fluorionophore).

Thus the test strip may be comprised in two possible combinations of components, the first combination being:

1a) an absorbent matrix through which the liquid containing the analyte to be measured is carried to a membrane.

2a) membrane affixed to and/or in contact with the matrix, said membrane containing
  a) certain lipophilic ions, each of which has a certain electrical charge;
  b) a chromoionophore (or fluorionophore) which is also adapted to carry a first ionic species into said membrane where said ionic species will neutralize a portion of the certain electrical charge of a portion of said lipophilic ions, and which will change color (or fluorescence) when it carries an ion into the membrane.
  c) A plurality of affinophores, each of which is adapted to carry into said membrane a second ionic species which after entering the membrane will neutralize the certain electrical charge of a portion of said lipophilic ions, and which possesses a binding affinity for a recognition molecule which binds to the substance being measured.

3a) a plurality of recognition molecules which bind both to the substance to be measured and to the affinophore, said recognition molecule being present on the absorbent matrix and/or added to or already present in the solution containing the analyte.

4a) a source of ions which will be transported by the chromoionophores (or fluorionophores) and affinophores, said ions being contained in the absorbent matrix and/or added to or already present in the solution matrix, the concentration of said ions available to the membrane being either controlled (e.g. buffered) or in excess.

The second combination of components comprising the test strips is 1b) an absorbent matrix through which the liquid containing the analyte to be measured is carried to a membrane.

2b) membrane affixed to and/or in contact with the matrix, said membrane containing
  a) certain lipophilic ions, each of which has a certain electrical charge;
  b) a plurality of chromaffinophores (or fluoraffinophores) each of which is adapted to carry an ion or ions to said membrane, and which will change color (or fluorescence) when it carries an ion into the membrane, and which possess a binding affinity for a recognition molecule which binds to the analyte being measured.

3b) a plurality of recognition molecules which bind to both the analyte to be measured and to the chromaffinophore (or fluoraffinophore), said recognition molecules being present on the absorbent matrix and/or added to or already present in the solution being measured.

4b) a source of ions which will be transported by the chromaffinophores (or fluoraffinophores) said ions being contained in the absorbent matrix and/or added to or already present in the solution matrix, the concentration of said ions available to the membrane being either controlled (e.g. buffered) or in excess.

Either of the above embodiments may be modified to incorporate the placement of a chemical marker at some point on the strip, said chemical marker providing a visible change resulting from exposure of the marker to the liquid which carries the sample. This marker serves to alert the user that the solvent front carrying the sample has reached the point at which the strip should be read.

According to a second aspect of the present invention, a method is provided to determine the concentration of a certain analyte occurring within a solution. When used with the embodiment of the apparatus which does not possess the ionic species impregnated into the absorbent matrix, the method comprises the following steps:

1) adding a specified quantity of recognition molecules and/or of ionic species and/or buffering compounds to a specified volume of sample.
2) Mixing the sample
3) Waiting a prescribed period of time greater than one (1) second and less than one (1) hour.
4) Placing a test strip of the type described in the first aspect of invention into a volume of a sample which is to be tested for a time sufficient to allow the sample to permeate the absorbent matrix and/or to chromatograph into the matrix, so as to bring the sample and recognition molecule into contact with the membrane, thereby allowing recognition molecules which are not bound to the analyte in the sample to bind to the affinophore or chromaffinophore (or fluoraffinophore) in the strip molecules, thereby affecting the color or the membrane in a manner related to the concentration of said analyte within said medium.
5) Stopping the flow of the sample into absorbant matrix either by removing the strip from the sample or by controlling the volume of sample so that the supply is exhausted.
6) Reading the test strip with the help of a calibrated scale provided with the test strip kit.

Additionally, according to a second aspect of the present invention, a second method is also provided to determine the concentration of a certain analyte occurring within a solution. This method will be used with the embodiment of the apparatus which possesses both the ionic species and the recognition molecules impregnated into the absorbent matrix. The method comprises the steps:

1) placing a test strip of the type described in the first aspect of the present invention into a volume of a sample which is to be tested for a time sufficient to allow the sample to permeate the absorbent matrix and/or to chromatograph into the matrix, so as to bring the sample and recognition molecule into contact with the membrane, thereby allowing recognition molecules which are not bound to the analyte in the sample to bind to the affinophore or chromaffinophore (or fluoraffinophore) in the strip molecules which are not bound to the analyte in the sample to bind to the affinophore or chromaffinophore (or fluoraffinophore) in the strip molecules, thereby affecting the color or the membrane in a manner related to the concentration of said analyte within said medium.
2) Stopping the flow of the sample into absorbant matrix either by removing the strip from the sample or by controlling the volume of sample so that the supply is exhausted.
3) Reading the test strip with the help of a calibrated scale provided with the test strip kit.

Third and fourth embodiments of the second aspect of the invention result in the case of strips which incorporate the placement of a chemical marker at some point on the strip, said chemical marker providing a visible change resulting from exposure of the marker to the liquid which carries the sample. This marker (hereafter referred to as "the end point marker") serves to alert the user that the solvent front carrying the sample has reached the point at which the strip should be read. For these strips, step 1 of the procedures becomes:

1) placing a test strip of the type described in the first aspect of the present invention into a volume of a sample which is to be tested for a time sufficient to allow the sample to permeate the absorbent matrix and/or to chromatograph into the matrix, so as to bring the sample and recognition molecule into contact with the membrane, thereby allowing recognition molecules which are not bound to the analyte in the sample to bind to the affinophore or chromaffinophore (or fluoraffinophore) in the strip molecules which are not bound to the analyte in the sample to bind to the affinophore or chromaffinophore (or fluoraffinophore) in the strip molecules, thereby affecting the color or the membrane in a manner related to the concentration of said analyte within said medium; said sufficient time being defined by a change in the end point marker.

Further objects, features, and advantages of the present invention will become apparent from a consideration of the following description and the appended claims when taken in conjunction with the accompanying drawings.

BRIEF DESCRIPTION OF THE DRAWINGS

For a fuller and more complete understanding of the nature and objects of the present invention, reference should now be made to the following drawings in which:

FIG. 2 is a top view of the apparatus shown in FIG. 1 illustrating the use of color generation to illustrate the determined concentration of metabolite within the medium of FIG. 1;

FIG. 5 is a front view of a birth management apparatus comprising an embodiment of the invention utilizing direct modulation with the recognition molecule in the solution.

FIGS. 6(a)–6(c) are top views (photographs) of birth management apparatus comprising embodiments of the invention where 1) the membrane is applied to the strip over a continuous region and 2) where the membrane is applied to the strip in a series of dots, both arrangements embodying the principles of the preferred embodiment of the invention; and FIG. 7 is a chemical reaction schematic diagram illustrating the synthesis of an affinophore utilized in the preferred embodiment of the invention.

DETAILED DESCRIPTION OF THE INVENTION

Figure 1:
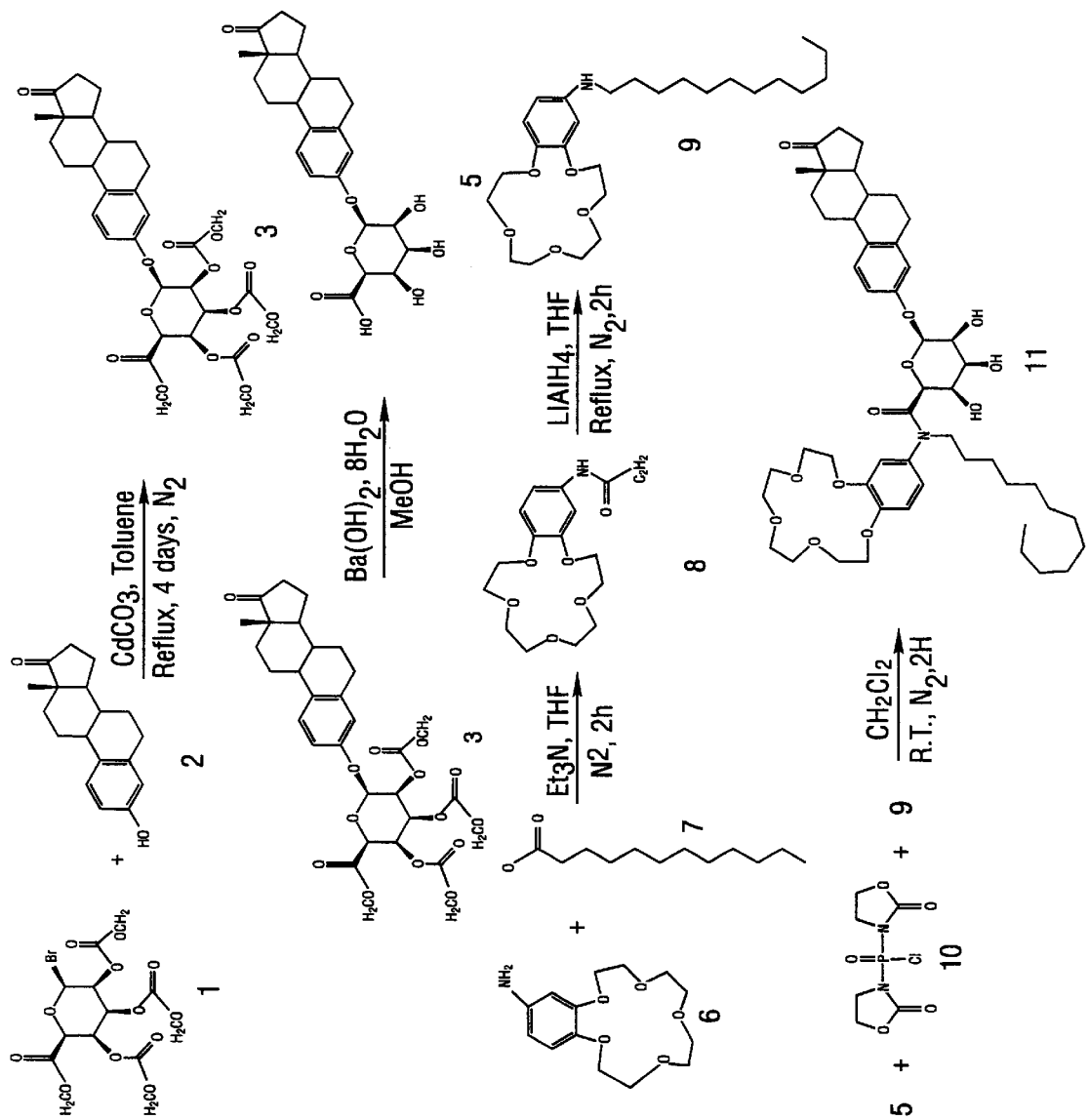
FIG. 1 is a front view of an apparatus made in accordance with the teachings of the preferred birth management embodiment of the invention and shown immersed within a medium. This embodies the indirect modulation with the recognition molecule on the strip.

Referring now to FIG. 1, there is shown an apparatus 10 for measurement of analyte concentration or presence, made in accordance with the teachings of the present invention and useful for birth management applications. It should be noted by those of ordinary skill in the art that the following discussion delineates methodological principles underlying and forming and integral part of Applicant's invention and that these principles may be used quite apart from the birth management technique which is hereafter discussed. As shown, apparatus 10 includes, on one side, a generally absorbent matrix 12, such as commercially available filter paper, onto which is placed a generally lipophilic membrane 14. In the preferred embodiment of the present birth management invention, the lipophilic membrane matrix 14 comprises such as and without limitation, a mixture of polyvinyl chloride, polyurethane and bis(2-ethylhexyl) sebacate and contains a plurality of chromoionophores 18, such as and without limitation ETH 5350 [9-(diethylamino)-5-[2-octyldecyl)imino]benzo[a]phenoxazine] each of which may be bound to a positively charged ion 20 such as and without limitation, hydrogen (H+), and capable of carrying the bound ion 20 from the interface between the membrane and the liquid permeating the absorbent matrix 12, into the interior of the membrane 14, and which changes color when bound to said ion. Said membrane also contains a plurality of affinophores 22, such as and without limitation, [2-dodecyl-2-methyl-1,3-propanediyl bis[N-5'-amido-estrone-3-glucuronidyl-(benzo-15-crown-5)-4'-yl] carbamate], each of which may be bound to a positively charged ion 24 such as, and without limitation, potassium- (K+), and capable of carrying said bound ion 24 from the interface between the membrane and the liquid in the absorbent matrix 12, into the interior of the membrane 14. Said membrane also contains a plurality of counter-ions 16, such as and without limitation, sodium tetrakis [3,5-bis (trifluoromethyl)phenyl]borate, the concentration of said anions being limited so that maintainance of charge neutrality within the membrane requires competition between chromoionophores 18 and affinophores 22.

Also in the preferred embodiment of the present invention, a plurality of recognition molecules 42, such as and without limitation, anti-estrone-3-glucuronide antibody, are deposited on the absorbent matrix 12 at a location between the membrane and the end of the absorbent matrix 12 which is to make contact with the sample. In an alternative embodiment, the plurality of recognition molecules 42 are deposited on the area of the absorbent matrix which contacts the membrane 14.

As should be apparent to one of ordinary skill in the art, chromoionophores 18 exhibit a first color, such as and without limitation, the color "blue" when carrying a positively charged ion such as and without limitation, H+ ion 20, and a second and different color, such as and without limitation, the color "pink" when not carrying this positively charged ion. Moreover, affinophores 22 for use in Applicant's techniques may be synthesized from commercially available ionophores through chemical and/or biological alteration or conjugation with or to a molecule which may comprise a binding molecule, such as and without limitation, an antigen identical to or resembling the analyte whose concentration is to be measured using an antibody as a biological recognition molecule, such as and without limitation estrone-3-glucuronide. Affinophores 22 may also be synthesized which are based upon ionophores which are not commercially available. The biological recognition molecules 42 may alternatively comprise a nucleotide sequence having a chemical and/or biological binding affinity for the analyte, a biological receptor for the analyte, an amino acid sequence which confers binding for the analyte, or virtually any substance which has some chemical and/or biological binding affinity for the analyte of interest. Upon binding to the biological recognition molecule, the affinophore's ability to bind and carry ions into the membrane is reduced and/or compromised and/or eliminated. It first must be realized that charge neutrality must be maintained within the membrane. Thus, a reduction in the number of charged ions carried by the affinophore must necessarily be compensated for by a concomitant increase in the number of charged ions carried into the membrane by the chromoionophore. Hence, the color of the membrane is shifted toward the color characteristic of the charge carrying chromoionophore.

Figure 8:
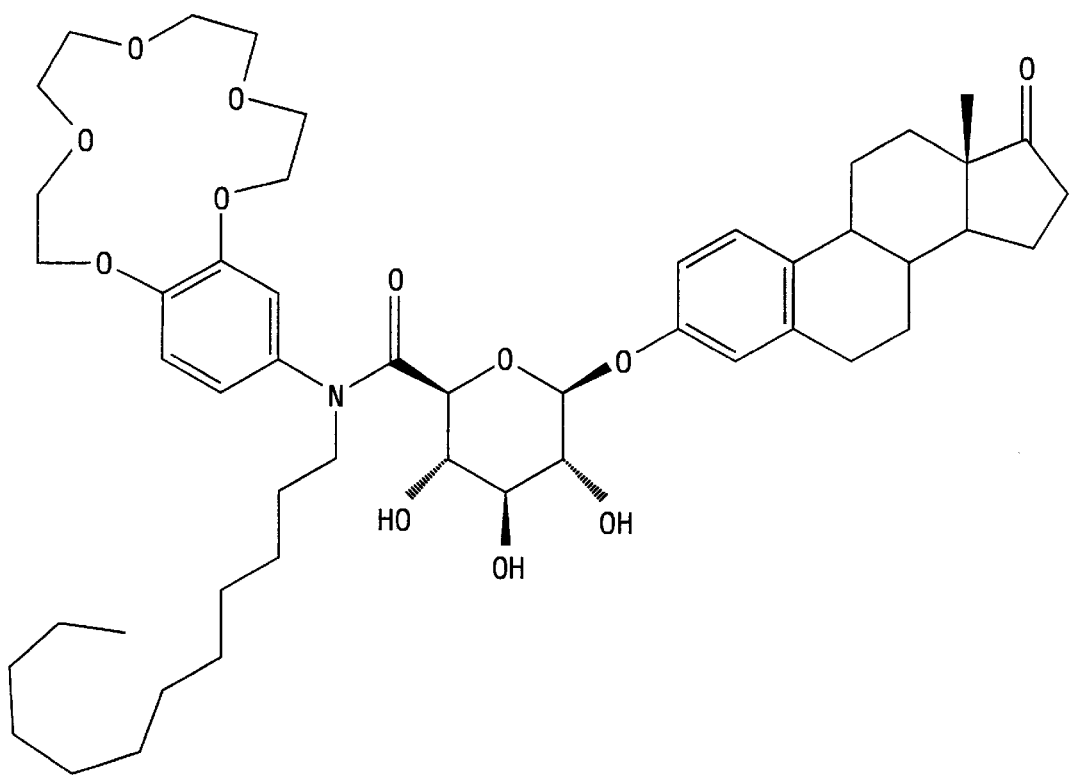
FIG. 8 shows the molecule, [2-dodecyl-2-methyl-1,3-propanediyl bis[N-5'-amido-estrone-3-glucuronidyl-(benzo-15-crown-5)-4'-yl]carbamate]], the affinophore molecule for Elg utilized in the preferred embodiment of the invention.

In the preferred birth management embodiment of Applicant's present invention, affinophore 22 comprises [2-dodecyl-2-methyl-1,3-propanediyl bis[N-5'-amido-estrone-3-glucuronidyl-(benzo-15-crown-5)-4'-yl] carbamate]. This is shown in FIG. 8. Particularly, in one embodiment of the birth management embodiment, the affinophore was synthesized by Applicants in the following manner and shown schematically in FIG. 7:

(1) Synthesis of Methyl [17-Oxaestra-1,3,5(10)-trien-3-yl-2',3',4'-tri-O-acetyl-D-glucopyranosid] uronate (3):

Toluene (300 ml) was added to a flame dried 500 ml three necked flask containing estrone 2 (1.67 g, 6.18 mmol) and cadmium carbonate (2.13 g, 12.36 mmol). A short path distillation assembly with a receiver was attached to one of the necks and the whole set up was kept under inert atmosphere. Toluene was distilled (25 ml) to ensure dryness to the contents of the flask. In another flame dried flask (100 ml) was taken bromo sugar [1-bromo-2',3',4'-tri-O-acetyl-D-glucopyranosid uronate] 1 (4.91 g, 12.36 mmol) in toluene (90 ml). This solution was added dropwise to a stirred mixture of estrone and cadmium carbonate for 1 h and an equal volume of toluene distilled from the flask at roughly the same rate. After the addition was complete, the distillation assembly was replaced by a reflux condenser and the mixture refluxed for 4 days. The mixture was filtered as a hot solution over a pad of celite, and the filtrate was evaporated to an oil. The oil obtained was crystallized by dissolving it in $CH_2Cl_2$ and adding absolute ethanol to the boiling solution. The resulting crystals were recrystallized from $CH_2Cl_2$—EtOH to obtain 3 as colorless crystals (2.33 g, 64%). Analytical material was obtained by further purification by flash chromatography [EtOAc-Hexane, 40–60% EtOAc]. Rf 0.56 (EtOAc:Hexane, 6:4).

IR (Kbr): 1758, 1498, 1226, 1100, 1053 cm-1.

1H NMR (CDCl$_3$): 0.9 (s, 3H, CH$_3$), 2.03 (s, 3H, OCOCH$_3$), 2.04, (s, 3H, OCOCH$_3$), 2.05 (s, 3H, OCOCH$_3$), 2.88 (m, 2H), 3.74 (s, 3H, COOCH$_3$), 4.16 (m, 1H, H-5), 5.09 (s, 1H), 5.11 (s, 1H), 5.32 (m, 4H), 6.73 (d, J=2.4 Hz, 1H), 6.78, 6.79 (dd, J=8.4 Hz, 2H), 7.21 (d, J=8.4 Hz, 1H).

(2) Hydrolysis of Acetylated Glycosides. 17-Oxoestra-1,3,5 (10)-trien-3-yl-β-D-glucopyranosid uronic acid (5):
To a suspension of 3 (0.1 g, 0.177 mmol) in CH$_2$Cl$_2$ (2 ml) was added Ba(OH)$_2$. 8H$_2$O (0.03 g, 0.097 mmol) in methanol (1.95 ml) added as a stock solution and let stir for 0.5 h. TLC shows complete conversion of the starting material. The solvents were evaporated and the residue dissolved in a mixture of EtOAc, ~0.05N HCl-saturated brine solution (1:1, 20 ml) and stirred for 5–10 minutes. The contents were transferred to a separatory funnel and the layers separated. The organic layers were washed with brine, dried over anhydrous MgSO4, filtered and concentrated to afford 5 as a flaky substance (0.89 g).

IR (KBr): 3422, 1727, 1498, 1245, 1086, 1033 cm-1.

(3) Synthesis of 4'-[N-Dodecanoylamino]benzo-15-crown-5 (8):
Dodecanoyl chloride 7 (1.7 g, 7.79 mmol, 1.8 ml) in 20 ml tetrahydrofuran (THF) was added dropwise to an anhydrous THF solution (40 ml) containing 4'-aminobenzo-15-crown-5 6 (2 g, 7.08 mmol) and triethylamine (1.58 g, 15.58 mmol, 2.17 ml) at room temperature and under nitrogen atmosphere. After the reaction was complete (2 h), the precipitate was filtered, and the filtrate concentrated to dryness in vacuo. The residue was dissolved in chloroform (75 ml), washed with water (25 ml), dried over MgSO$_4$, filtered and concentrated. The crude solid obtained was recrystallized from ethanol to obtain 1.5 g of colorless crystals. The filtered precipitate was dissolved in water (25 ml) and chloroform (75 ml) and extracted. The organic layers were washed with water (25 ml) and brine (25 ml), dried over MgSO4, filtered and concentrated to obtain a solid (1.51 g) which corresponded to the pure recrystallized product 8 by TLC and 1H NMR. Both of the products were combined to obtain 8 (3.01 g, 91% yield).

IR (KBr): 3286, 1656, 1516, 1241, 1141 cm-1.

1H NMR (CDCl$_3$): 0.87 (t, J=6.5, 7.5 Hz, 3H), 1.25 (m, 16H), 1.7 (m, 2H), 2.31 (t, J=7.5 Hz, 2H), 3.75 (d, J=3 Hz, 8H), 3.88 (q, 4H), 4.12 (m, 4H), 6.8 (d, J=1.5 Hz, 2H), 7.12 (s, 1H, NH), 7.38 (d, J=1.5 Hz, 1H).

(4) Synthesis of 4'-[N-Dodecylamino]benzo-15-crown-5 (9) Compound 8 (2.9 g, 6.29 mmol) in anhydrous THF (90 ml) was treated with lithium aluminum hydride (0.72 g, 18.87 mmol) and refluxed for 4 h. After the reaction mixture was cooled in an ice bath, excess LiAlH$_4$ was carefully decomposed in chloroform (75 ml), washed with water (20 ml), brine (20 ml), dried over MgSO$_4$, filtered and concentrated. TLC and 1H NMR show presence of no other products or impurities and the compound (9) obtained was used as such. [2.86 g, quantitative] Rf 0.5 (EtOH:CHC13, 6:94).

IR (KBr): 1518, 1230, 1130, 1106, cm-1.

1H NMR (CDCl$_3$): 0.87 (t, J=6.6, 6.9 Hz, 3H), 1.26 (s, 18H), 1.59 (m, 2H), 3.03 (t, J=7.2, 6.6 Hz, 2H), 3.75 (s, 8H), 3.88 (m, 4H), 4.08 (m, 4H), 6.13 (dd, J=8.7, 8.4 Hz, 1H), 6.21 (d, J=2.7 Hz, 1H), 6.77 (d, J=8.4 Hz, 1H).

(5) Coupling reaction between 5 and 9 with BOP—Cl (10): In a flame dried (100 ml) flask were taken 5 (0.89 g, 0.19 mmol), 9 (0.07 g, 0.15 mmol) and triethylamine (0.03 g, 0.04 ml) in anhydrous THF (20 ml). In another flask was taken BOP—Cl 10 (0.3 g) dissolved in a mixture of anhydrous THF (16 ml) and CH2C12 (5 ml). From this, an aliquot (2.8 ml, 0.15 mmol) was taken and added dropwise to the above flask containing compounds 5 and 9 at room temperature and left stirring overnight (~10 h). Water (10 ml) was added and stirred for 5 minutes and the solvents were evaporated under vacuum. EtOAc (50 ml) was added and the layers separated, the organic layers were washed with brine (20 ml), dried over MgSO$_4$, filtered and concentrated. The residue obtained was purified by gravity column using silica gel (100–200 mesh) and eluting with a gradient of EtOH—CHCl$_3$ (2–8% EtOH). Unreacted 4'-[N-dodecylamino]benzo-15-crown-5 (9) (0.055 g) followed by the pure adduct 11 (0.015 g, 51% based on the consumption of 8. Rf 0.24 (EtOH:CHCl$_3$, 6:94).

IR (KBr) 3385, 1736, 1514, 1265, 1128, 1056 cm-1.

1H NMR (CDCl$_3$): 0.88 (t, 3H, terminal CH$_3$), 0.92 (s, 3H, c-13 CH$_3$), 1.25 (s, alkyl chain), 3.74 (s, 8H), 3.86 (m, 4H), 4.07 (m, 4H), 6.68, 6.71, 6.79, 6.85, 7.19 (aromatic).

In the synthesis reported above, the appearance of the peak in the IR at 1265 suggests that side reaction has occurred between BOP—Cl and the hydroxyls of the steroid glucuronide. BOP—Cl was used in the previously described method because coupling was occurring between a secondary amine and a carboxyl group. By changing the starting material so that a primary amine is used, it becomes possible to utilize decyclohexylcarbodiimide in place of BOP—Cl as the coupling agent. It is expected that this will eliminate the suspected side reaction. The synthesis will instead proceed from 4'-amino-5'-nitrobenzo-15-crown-5. The amine will be reacted with dodecanoyl chloride, placing the dodecyl moiety at the 4' nitrogen. The amide and the 5'-nitro group could then be reduced in a single step with either sodium borohydride and titanium tetrachloride or sodium borohydride and cobalt chloride hexahydrate to afford 4'-dodecylamino-5'-aminobenzo-15-crown-5. If the single step reduction of both the nitro and amide is not successful, they could be reduced step wise with lithium aluminumhydride for the amide group followed by the reaction of nitro group with 10% palladium on carbon under hydrogen. The coupling to the steroid glucuronide will then proceed using dicyclohexylcarbodiimide as the coupling agent rather than BOP—Cl.

It should be realized by one of ordinary skill in the art that while the aforementioned affinophores was employed in this birth management embodiment, other types of affinophores may be utilized. In general, an affinophore for use in Applicants' techniques as earlier stated are entities having a binding affinity for the metabolite of interest and the ability to carry an ion into a lipophilic membrane.

Referring now to FIGS. 6(a)–6(c), there are shown strip tests made in accordance with the principles of the preferred embodiment of the present invention. Specifically, the apparatus 10 comprises a strip of Whatman chromatography paper grade 20 which had dimensions of about 4 mm×10 cm in this embodiment, about 3 μl of membrane solution was spread on the surface of the strip in an area occurring between about 2.5 cm to about 4.0 cm from the bottom of the strip. About 1.0 μl of antibody solution was placed in a stripe upon the strip matrix at a point about 2 cm from the bottom of the strip.

Moreover, in the preferred birth management embodiment the membrane solution was prepared which utilized chemicals (obtained from Fluka, Ronkonkoma, N.Y.) in the following amounts: 200 μl of a solution comprising about 20 mg of polyvinyl chloride (high molecular weight), 40 mg of bis(2-ethylhexyl) sebacate and about 1 ml of redistilled tetrahydrofuran, about 0.0038 mmole of ETH 5350 [9-(diethylamino)-5-[2-octyldecyl)imino]benzo[a]phenoxazine] chromoionophore III per kg of PVC/DOS (1:2) and an amount of the lipophilic anion, sodium tetrakis [3,5-bis(trifluoromethyl)phenyl]borate, and the aforedescribed affinophore, sufficient to create a substance ratio of about 1:1.1:10 of chromoionophore to anion to affinophore. (This formulation is referred to as batch 1 in FIG. 6). A second formulation referred to as batch 2 comprises the following: 200 µl PVC/DOS (20 mg PVC +40 mg DOS in 1 ml. THF), 10 µl of sodium tetrakis [3,5-bis (trifluoromethyl)phenyl]borate (1.67 mg/ml of THF and 100 µl of ETH 5350 chromoionophore III (100 µl of ETH 5350 flourionophore III can be substituted for the 100 µl of ETH 5350 chromoionophore III) (1.167 mg/ml of THF and 100 µl of the affinophore (4 mg/200 µl THF).

The antibody was anti-estrone-3-glucuronide monclonal antibody clone #278-17144 which was obtained by and through OEM Concepts, Inc. of Toms River, N.J. The solution contained about $2 \times 10^{-9}$ moles of antibody in about 1.0 µl of 0.1M bis-tris propane buffer having a pH of about 7.002.

When all of the solutions had dried on the strip, the strip was mounted vertically so that its bottom touched the bottom of a well of an ELISA plate, the strip being held perpendicular to the well. The strip did not contact any other surface below the mounting point. About 40 µl of 0.1M bis-tris propane buffer having a pH of about 7.002 was placed into the well and allowed to rise up the strip chromatographically, distributing the antibody over the surface of the membrane where it is bound by the affinophore. About 10µl of the sample to be measured was added to about 1 ml of about 0.1M KCl in about 0.1M bis-tris propane buffer, having a pH of about 7.0. About 20µl of this solution was chromatographed up the strip and the height at which the strip changed from blue to pink correlated with the concentration of estrone-3-glucuronide in the sample. Example strips demonstrating about 20 ng and about 80 ng of estrone-3-glucuronide samples and also tests on actual urine samples collected during the ovulatory and non-ovulatory phases are shown in FIGS. 6(a)–6(c).

In order for apparatus 10 to reliably indicate the concentration of the desired metabolite within medium 30, the ion concentration within the medium must be controlled. Two control methods include, without limitation, maintaining the ions present in sufficient excess over the amounts of affinophore and chromaffinophore (or fluoraffinophore) in the apparatus 10 so that variations in the actual concentrations of the ions in the medium produce substantially no significant change in the amount of the ions transported to and within membrane 14 and/or buffering the ion concentrations in the medium by the use of commercially available pH or metal buffers so as to insure that the available free ions within the solution remain substantially constant.

As shown in FIGS. 1 and 2, one end of apparatus 10 is adapted to be immersed within medium 30 containing analyte 40. In operation, the affinophores 22 compete with the chromoionophores (or fluorionophores) 18 for a limited amount of counter-ion 16. Upon entry into the membrane, ions 20 and 24, respectively carried into membrane 14 by chromoionophores (or fluorionophores) 18 and affinophores 22, neutralize corresponding counter-ions 16. Since the membrane 14 must remain electrically neutral, the amount of counter-ions 16 determines the overall amount of affinophores 22 and chromoionophores (or fluorionophores) 18 which may carry ions 20 and 24 into the membrane 14 at any instant in time. Hence, there is a competition between affinophores 22 and chromoionophores (or fluorionophores) 18 for entry of their respective ions into the membrane. However, the use of biological recognition molecules 42 "skews" this competition in favor of the chromoionophores (or fluorionophores) 18, by an amount which is proportional to the concentration of metabolite 40 occurring within the medium 30. In essence, a first substance (ions 20 carried by chromoionophores (or fluorionophores) 18) competes with a second substance (ions 24 carried by affinophores 22) for entry into the membrane 14 in order to neutralize the charge on the plurality of counter-ions 16. The biological recognition molecules 42 (third substance) modulates this competition by attaching to and/or binding with a portion of the affinophores 22, thereby preventing the bound affinophores (such as affinophore 26 which is shown in FIG. 1) from carrying an ion into membrane 14. In this manner, more of the counter-ions 16 are available for the chromoionophores (or fluorionophores) 18 to neutralize. Hence, more ion containing chromoionophores (or fluorionophores) 18 enter the membrane 14 than would enter without the presence of the biological recognition molecules 42, thereby causing a shift in the ion concentration at which a color change occurs in the chromoionophores (or fluorionophores) 18. A mathematical description of these relationships is set forth in the set of equations found in the article entitled "Selectivity of Ion-Sensitive Bulk Optodes", which was authored by E. Bakker and W. Simon, which appeared in Volume 64 on pages 1805–1812 of the journal entitled *Analytical Chemistry*, published in 1992, which is fully and completely incorporated herein by reference, word for word and paragraph for paragraph. In practice, the color of the matrix 12 will correspond to that of the chromoionophore (or fluorionophore) when $L_{tot}$ (as defined in the aforementioned article in *Analytical Chemistry* to be the concentration of ion-selective ionophore in the membrane) is at a maximum. These biological recognition molecules 42 bind first to the analyte 40 occurring in the medium, with the remainder binding to the affinophores 22. In this manner, one may calibrate the increase in chromoionophore (or fluorionophore) entry into membrane 14 since it is proportional to the amount of analytes 40 existing within the solution medium 30. Moreover, the amount of biological recognition molecules attached to the various affinophores 22 is inversely proportional to the amount of analytes 40 existing or occurring within the medium 30.

When the end of apparatus 10 is placed into the medium 30, antibody of biological recognition molecules 42, which have not been bound to the analyte molecules in the sample 30 will be bound to the affinophores 22, in the manner previously discussed, thereby allowing more chromaffinophores (or fluoraffinophores) 18 to carry ions 20 into the membrane 14. In the preferred embodiment of the present invention, the bottom of apparatus 10 will be placed in an amount of diluent sample liquid sufficient to rise chromatographically up the strip to a predetermined level. As the chromoionophore (or fluorionophore) enters the membrane 14, color changes occur along the matrix 12 (as shown in FIG. 2). At some point along the strip, a sufficient amount of antibody 42 will have been bound so the amount remaining which binds to the region of the strip is not sufficient to cause the strip to change color. This point will divide strip matrix 12 into two regions 60, 70. The amount of antigen or analyte which causes this to occur at various points along a calibration scale 80 along strip matrix 12 will be calibrated so that the concentration can be read, in a relatively easy manner, by the division point along the strip 12. Hence, the strip test of this invention or "home-based" testing technique utilizes a distinct transition from one color to another, such as commonly seen with pH indicators, as the visual signal must be recognized. Quantification of the response will be accomplished spatially in a manner similar to that of a thermometer. The individual reading of the strip will simply compare the location along the strip where the color change occurs with a calibration scale (such as 80) on the side of the strip 12. The method of this embodiment of the present invention will require no "rinse" steps and the components of the strip matrix 12 are considerably more stable than enzymes which are used in prior techniques.

Figure 3:
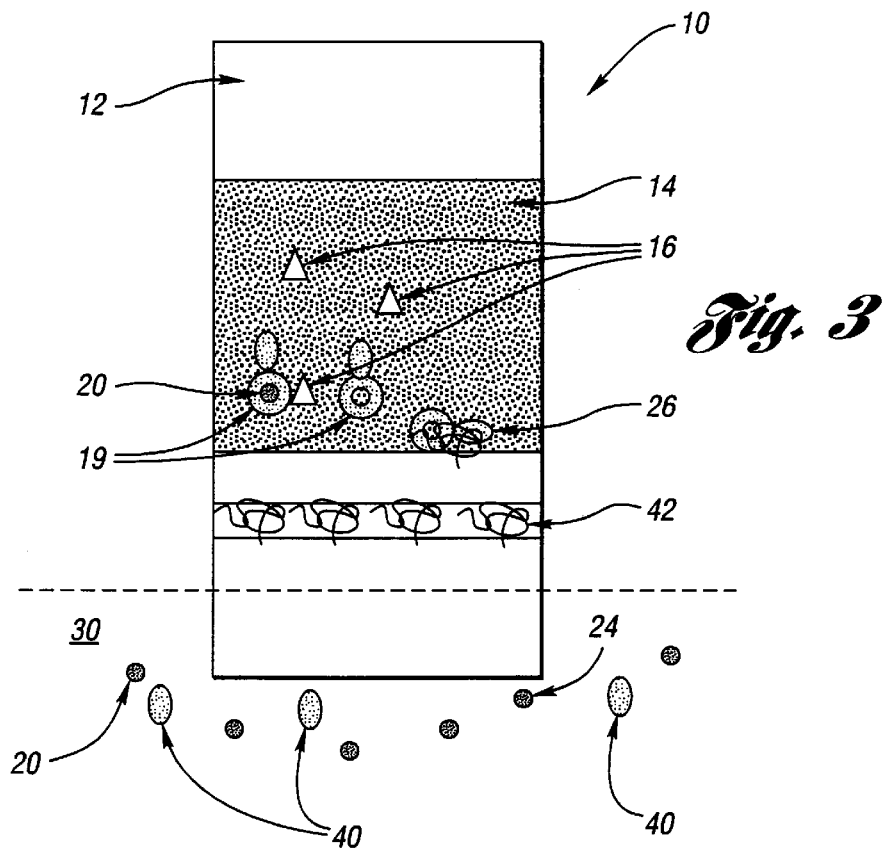
FIG. 3 is a front view of a birth management apparatus comprising an embodiment of the invention utilizing direct modulation and recognition molecule impregnated on the strip.

In a second embodiment of the present birth management invention, shown in FIG. 3, the chromoionophore (or fluorionophore) 19 is chemically and/or biologically attached to a molecule having a binding affinity for the biological recognition molecule, the molecule conjugate hereinafter referred to as a "chromaffinophore (or fluoraffinophore)". In this embodiment, there is no competing ionophore or affinophore. When the recognition molecule 42 binds to the chromaffinophore (or fluoraffinophore) 19, the chromaffinophore (or fluoraffinophore) portion is obstructed by the relatively large biological recognition molecule (as shown by 26). This alters the chromaffinophore (or fluoraffinophore)'s ability to chemically interact with the counter-ion 16 to which it responds. Hence, the amount of binding of the recognition molecule to the chromaffinophore (or fluoraffinophore) is inversely proportional to the amount of metabolite within the medium 30. Moreover, it should be appreciated by one of ordinary skill in the art that each of the embodiments may be used to simply change color (without the aforedescribed calibration strip portion) to indicate the presence of the metabolite, and that various types of metabolites may be detected in presence or concentration, including and without limitation, pregnanediol-glucuronide, estrone 3-glucuronide and estriol glucuronide.

Figure 4:
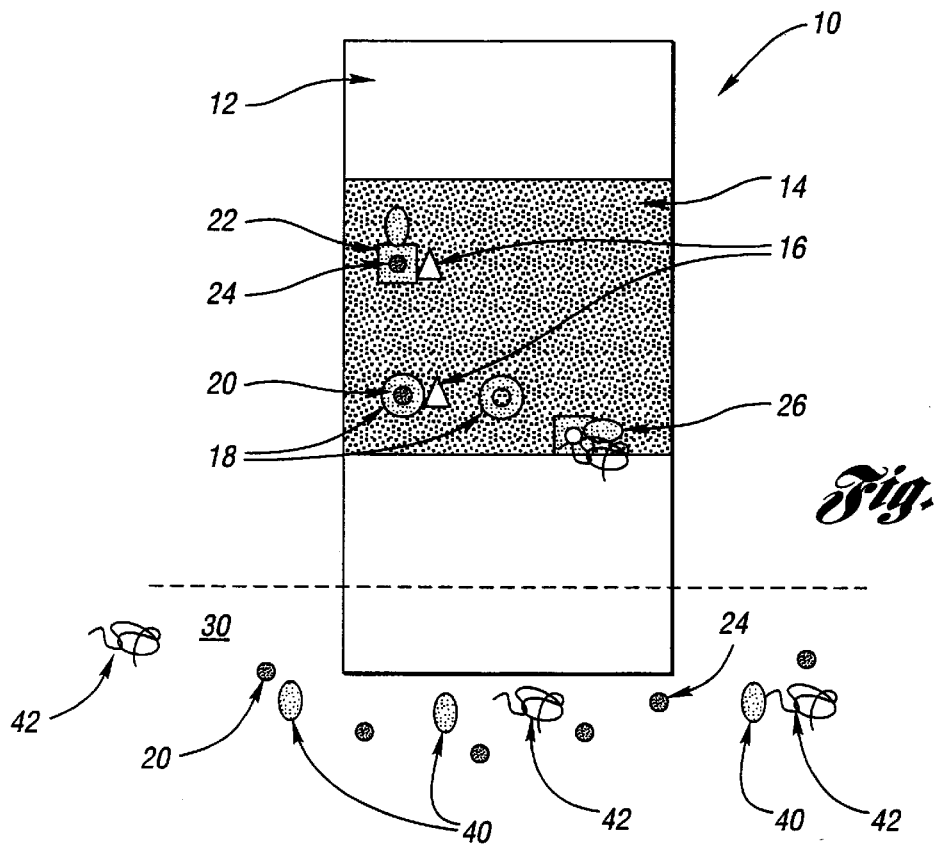
FIG. 4 is a front view of a birth management apparatus comprising an embodiment of the invention utilizing indirect modulation with the recognition molecule in the solution.

Moreover, in third and fourth embodiments of the present invention, the recognition molecule is placed in the sample rather than on the test strip, in each of these embodiments which, in all other ways, respectively correspond to the first and second embodiments of the invention (as shown in FIGS. 4 and 5).

In a fifth variation of the preferred embodiment of the present invention, the affinophore test strip placed the membrane solution in a series of about 1 micro-liter dots which were spaced at about 2.5, 3.25, and about 4 cm from the bottom of the strip. This facilitates visualization in terms of the number of dots that have become pink rather than a continuous field with a demarcation line between blue and pink. All other procedures remained the same. This is shown in FIG. 6, examples b and c.

It is to be understood that the invention is not limited to the exact construction and modifications illustrated and described above, but that various changes and modifications may be made without departing from the spirit and the scope of the invention as defined in the following claims.

It should be realized by one of ordinary skill in the art that what has been disclosed is one embodiment of a novel technique which is a new and useful type of visual immunoassay, one based upon affinophores, which obviates the need for prior costly techniques such as radioisotope type immunoassays or enzyme linked antibody assays. Moreover, it should be further apparent that the aforedescribed birth management invention is both relatively inexpensive and relatively easy to use, thereby having great utility as a "home-based" birth management system and as a veterinary means of monitoring animal fertility. It should also be realized that the use of such affinophore binding allows concentrations of metabolites to be sensed in much smaller concentration amounts than previously possible with "home-based" techniques.

We claim:

1. A test apparatus for determining the presence of an analyte in a solution or an aqueous sample, said apparatus comprising:

(a) a buffered reagent comprising a first and second ion species;
(b) a biological recognition molecule which specifically binds to said analyte and an analog thereof;
(c) an absorbent matrix, said matrix interfaced with
(d) a lipophilic membrane comprising:
(i) a lipophilized chromoionophore which selectively binds to and transports said first ion species into said membrane, said chromoionophore changing from a first color to a second color upon selective binding to said first ion species,
(ii) an affinophore which specifically binds to said biological recognition molecule and comprising said analyte or said analog thereof conjugated to an ionophore which selectively binds to and transports said second ion species into said membrane, and
(iii) a lipophilic counter-ion present in an amount sufficient to maintain within said membrane a condition of ion exchange between said first ion species and said second ion species,
wherein said specific binding of the biological recognition molecule to said affinophore alters the selective binding and transport of the second ion species into said membrane, thereby increasing the selective binding and transport of the first ion species into said membrane to maintain the balance of charge within said membrane such that the presence or amount of said second color in said membrane is inversely proportional to the presence or amount of said analyte in the sample.

2. The test apparatus of claims 1 wherein said biological recognition molecule is an antibody.

3. The test apparatus of claim 1 wherein said biological recognition molecule is a portion of a whole antibody containing a binding site.

4. The test apparatus of claim 1 wherein said biological recognition molecule is a biological receptor for the analyte.

5. The test apparatus of claim 1 wherein said biological recognition molecule is a portion of a specific nucleotide sequence having an affinity for the analyte.

6. The test apparatus of claim 1 wherein said analyte is estrone-3-glucuronide.

7. The test apparatus of claim 1 wherein said analyte is pregnanediol-glucuronide.

8. The test apparatus of claim 1 wherein said analyte is estriol-glucuronide.

9. The test apparatus of claim 1 wherein the first ion species is H+, said second ion species is K+, the chromoionophore is 9-(diethylamino-5-[(2-octlydecyl)imino)]-5H-benzo[a]phenoxazine (ETH 5350), the lipophilic counter-ion is sodium tetrakis [3,5-bis(triflouromethyl) phenyl]borate, the affinophore is [2-dodecyl-2-methyl-1,3-propanediyl bis[N-5'-amido-estrone-3-glucuronidyl-(benzo-15-crown-5)-4'-yl]carbamate] and the analyte is estrone-3-glucuronide.

10. A test apparatus for determining the presence of an analyte in a solution or an aqueous sample, said apparatus comprising:

(a) a buffered reagent comprising an ion species;
(b) a biological recognition molecule which specifically binds to said analyte and an analog thereof;
(c) an absorbent matrix, said matrix interfaced with
(d) a lipophilic membrane comprising:
(i) a lipophilized chromaffinophore which specifically binds to said biological recognition molecule and comprising said analyte or said analog thereof conjugated to an ionophore which selectively binds to and transports said first ion species into said membrane, said chromaffinophore changing from a first color to a second color upon selective binding to said first ion species, and (ii) a lipophilic counter-ion present in an amount sufficient to enable transport of said first ion into said membrane, wherein said specific binding of the biological recognition molecule to said chromaffinophore alters the selective binding and transport of the first ion species into said membrane, such that the presence or amount of said second color in said membrane is inversely proportional to the presence or amount of said analyte in the sample.

11. The test apparatus of claim 10 wherein said biological recognition molecule is an antibody.

12. The test apparatus of claim 10 wherein said biological recognition molecule is a portion of a whole antibody containing a binding site.

13. The test apparatus of claim 10 wherein said biological recognition molecule is a biological receptor for the analyte.

14. The test apparatus of claim 10 wherein said biological recognition molecule is a portion of a specific nucleotide sequence having an affinity for the analyte.

15. The test apparatus of claim 10 wherein said analyte is estrone-3-glucuronide.

16. The test apparatus of claim 10 wherein said analyte is pregnanediol-glucuronide.

17. The test apparatus of claim 10 wherein said analyte is estriol-glucuronide.

18. The test apparatus of claim 10 wherein the ion species is H+, the lipophilic counter-ion is sodium tetrakis [3,5-bis (triflouromethyl)phenyl]borate, and the analyte is estrone-3-glucuronide.

* * * * *

UNITED STATES PATENT AND TRADEMARK OFFICE
CERTIFICATE OF CORRECTION

PATENT NO.    : 6,046,008
DATED         : April 4, 2000
INVENTOR(S)   : Erb et al.

It is certified that error appears in the above-identified patent and that said Letters Patent is hereby corrected as shown below:

<u>Column 1,</u>
Line 5, -- This invention was made with government support under contract DAMD17-96-C-6026 awarded by the Navy. The government has certain rights in the invention. --

Signed and Sealed this

Thirtieth Day of October, 2001

*Attest:*

*Nicholas P. Godici*

*Attesting Officer*

NICHOLAS P. GODICI
*Acting Director of the United States Patent and Trademark Office*